United States Patent [19]

Gauthier-Lafaye et al.

[11] Patent Number: 4,618,460
[45] Date of Patent: Oct. 21, 1986

[54] PROCESS FOR THE PREPARATION OF ACETIC ANHYDRIDE

[75] Inventors: Jean Gauthier-Lafaye, Lyons; Robert Perron, Charly, both of France

[73] Assignee: Rhone-Poulenc Industries, Courbevoie, France

[21] Appl. No.: 585,625

[22] Filed: Mar. 7, 1984

Related U.S. Application Data

[63] Continuation of Ser. No. 331,809, Dec. 17, 1981, abandoned.

[30] Foreign Application Priority Data

Dec. 24, 1980 [FR] France ................... 80 27942

[51] Int. Cl.$^4$ .............................................. C07C 51/56
[52] U.S. Cl. ..................................................... 260/549
[58] Field of Search ......................................... 260/549

[56] References Cited

U.S. PATENT DOCUMENTS

| | | | |
|---|---|---|---|
| 2,789,137 | 4/1957 | Reppe et al. | 260/549 |
| 4,002,677 | 1/1977 | Naglieri et al. | 260/549 |
| 4,002,678 | 1/1977 | Naglieti et al. | 260/549 |
| 4,134,912 | 1/1979 | Naglieri et al. | 562/579 |
| 4,239,698 | 12/1980 | Isshiki et al. | 260/549 |
| 4,351,953 | 9/1982 | Gauthier-Lafaye | 562/519 |

FOREIGN PATENT DOCUMENTS 18927  11/1980  European Pat. Off. .

OTHER PUBLICATIONS

*Lange's Handbook of Chemistry,* 12th Ed. (1979) McGraw-Hill, Publ. pp. 4-40, 4-94 and 4-111.
Onouchi, Takeshi et al., *Chemical Abstracts,* vol. 80 (1974) #107,994f.
Gauthier-Lafaye, Jean et al., *Chemical Abstracts,* vol. 94 (1981) #156,327p.
Falbe, Jurgen, "Carbon Monoxide in Organic Synthesis" (1970) p. 113, Springer, Publ.

*Primary Examiner*—Natalie Trousof
*Assistant Examiner*—L. Hendriksen
*Attorney, Agent, or Firm*—Burns, Doane, Swecker & Mathis

[57] ABSTRACT

The invention relates to a process for the preparation of acetic anhydride by carbonylation. In the process, carbon monoxide is reacted with methyl acetate in the liquid phase, in a carboxylic acid, in the presence of an effective amount of nickel, methyl iodide, an ionic iodide selected from the group consisting of quaternary ammonium iodides, quaternary phosphonium iodides, sodium iodide, potassium iodide and cesium iodide, and a co-catalyst selected from the group consisting of lithium salts and alkaline earth metal salts.

26 Claims, No Drawings

PROCESS FOR THE PREPARATION OF ACETIC ANHYDRIDE

This application is a continuation of application Ser. No. 331,809, filed Dec. 17, 1981, now abandoned.

CROSS-REFERENCE TO RELATED APPLICATION

Gauthier-Lafaye et al copending application Ser. No. 331,828, filed concurrently herewith, assigned to the assignee hereof, and expressly incorporated by reference herein and now abandoned.

BACKGROUND OF THE INVENTION

1. Field of the Invention

The present invention relates to a process for the preparation of acetic anhydride by the carbonylation of methyl acetate.

2. Description of the Prior Art

It is well known that acetic anhydride can be produced by the carbonylation of methyl acetate under relatively severe pressure conditions, in the presence of nickel complexes of the formula $$[A_4M]_2NiX_4$$

in which X represents a bromine or iodine atom, M represents a phosphorous or nitrogen atom and A is, for example, a lower alkyl radical; compare U.S. Pat. No. 2,729,651. These complexes, which are obtained by reacting nickel halides with quaternary phosphonium or ammonium halides, can be used in this form in the reaction in question, or alternatively they can be formed in situ. However, the efficiency of this type of process is low, despite the high pressures used.

More recently, catalyst systems have been proposed which make it possible to carbonylate methyl acetate under less severe pressure conditions. Thus, U.S. Pat. No. 4,002,678 describes the carbonylation of methyl acetate in the presence of nickel, chromium, iodine (or an iodine compound) and a phosphine (or an amine), under a pressure of less than 70 bars.

At the same time, it has been shown that chromium is not necessary in a process of this type if the reaction is carried out in an aliphatic carboxylic acid as the solvent, and provided that the iodine (or the iodine compound) is used in the reaction in a proportion such that the fraction of iodine which is not chemically bonded either to the nickel or to the promoter (phosphine or amine) is at least 0.2 mol (of elementary iodine) per mol of both the nickel compound and the promoter; compare British Patent Application No. 2,007,666.

Nevertheless, the industrial-scale development of these recent techniques, the value of which is not contested in principle, seems to be jeopardized because of the relatively low efficiency of the catalyst systems in question. An additional obstacle to the development of this type of process lies in the essential use of phosphines (or amines), the instability and cost of which detract from the overall economy of the processes.

SUMMARY OF THE INVENTION

It has now been found not only that it is possible to increase the efficiency of such prior art catalyst systems based on nickel, but also that it is not necessary, under certain conditions, to use phosphines or amines in order for the systems in question to develop an appreciable activity.

The present invention thus relates to a process for the preparation of acetic anhydride by the carbonylation of methyl acetate in the liquid phase, in a carboxylic acid, in the presence of an effective amount of nickel, methyl iodide, an ionic iodide selected from the group consisting of quaternary ammonium iodides, quaternary phosphonium iodides, sodium iodide, potassium iodide and cesium iodide, and a co-catalyst selected from the group consisting of lithium salts and alkaline earth metal salts.

DETAILED DESCRIPTION OF THE INVENTION

The process according to the invention requires the presence of an effective amount of nickel. Any source of nickel can be used within the scope of the present process. The nickel can be introduced in the form of the metal itself (for example, RANEY nickel) or in any other convenient form. The following may be mentioned as examples of nickel compounds which can be used to carry out the present process: nickel carbonate, oxide, hydroxide, halides, in particular iodide, and carboxylates, in particular acetate. Nickel tetracarbonyl and bis-(triphenylphosphine)-nickel dicarbonyl are also suitable.

The precise amount of nickel is not critical, just so long as an effective amount is employed. The proportion of nickel, which influences the reaction rate, is determined as a function of that reaction rate which is considered to be suitable, taking into account the other reaction parameters. Generally speaking, an amount of between 5 and 2,000 milligram atoms of nickel per liter of solution leads to satisfactory results. The reaction is preferably carried out with a proportion of between 20 and 1,000 milligram atoms of nickel per liter.

In order to carry out the present invention, the presence of methyl iodide in the reaction medium is also required. It is not necessary for this component of the catalyst system to be introduced initially and it is possible, for example, to use free iodine, hydriodic acid, an alkyl iodide which is different from methyl iodide, or an acyl iodide. As is known to those skilled in the art, iodine and these types of iodine compounds can be considered as precursors of methyl iodide in the reaction in question.

In general, methyl iodide is present in the reaction medium in an amount of 1 to 100 mols and preferably in an amount of 3 to 50 mols per gram atom of nickel present in the medium.

The catalyst system used within the scope of the present process also comprises an ionic iodide selected from the group consisting of quaternary ammonium iodides, quaternary phosphonium iodides, sodium iodide, potassium iodide and cesium iodide.

The precise nature of the quaternary phosphonium (or ammonium) iodides is not of fundamental importance and the choice from among these compounds is governed chiefly by considerations of a practical nature, such as availability, convenience of use and solubility in the reaction medium. In this respect, use of the quaternary ammonium or phosphonium iodides whose cations are represented respectively by formulas (I) and (II) below $$R_1N^+(R_2)_3 \qquad (I)$$

$$R_1P^+(R_2)_3 \qquad (II)$$

in which $R_1$ and $R_2$, which can be identical or different, represent linear alkyl radicals having at most 4 carbon atoms, it also being possible for $R_2$ to represent a phenyl, tolyl or xylyl radical, is recommended.

Examples which may be mentioned of quaternary ammonium iodides suitable for carrying out the present process are tetramethylammonium, triethylmethylammonium, tributylmethylammonium, tributyl-(n-propyl)-ammonium, tetraethylammonium and tetrabutylammonium iodides.

Examples which may be mentioned of quaternary phosphonium iodides suitable for carrying out the present process are methyltriphenylphosphonium, ethyltriphenylphosphonium, methyltrixylylphosphonium and methyltributylphosphonium iodides.

Of course, this type of compound, which must be present in order to carry out the present invention, can be formed in situ from the corresponding amine or phosphine introduced, if appropriate, in the form of a nickel complex such as bis-(triphenylphosphine)-nickel dicarbonyl, and from an alkyl iodide. If this procedure is chosen it will be appropriate to introduce, in addition to the amine (or phosphine) in question, the amount of alkyl iodide (if appropriate, methyl iodide) required for its quaternization, so that this conversion in situ does not take place to the detriment of the methyl iodide, which must also be present in the reaction medium.

Quaternary phosphonium iodides are especially suitable for use in carrying out the present process.

As indicated above, the ionic iodide can alternatively be selected from the group consisting of sodium iodide, potassium iodide and cesium iodide. Of course, as those skilled in the art will easily understand, it is not necessary to introduce the iodides of these metals initially, because they can be formed in situ from methyl iodide (or its precursors mentioned hereinabove) and, for example, from a carboxylate of the metal in question. It is self-evident that, again, this conversion in situ must not take place to the detriment of the methyl iodide, which must be present in the reaction medium, and that the remark made in respect of the preparation of the quaternary phosphonium (or ammonium) iodides in situ also applies to the case of the other ionic iodides.

In an advantageous variant of the present process, sodium iodide, potassium iodide or cesium iodide is used.

If the cation of the ionic iodide is designated by $M_1$, then the amount of ionic iodide which is generally present in the reaction medium is such that there are from 0.5 to 100 and preferably from 0.8 to 40 gram ions of $M_1$ per gram atom of nickel also present in the reaction medium. The ratio $M_1/Ni$ is advantageously between 1 and 20.

Finally, in the present process, it is essential to carry out the reaction in the presence of a co-catalyst selected from the group consisting of lithium salts and alkaline earth metal salts.

Both inorganic salts and organic salts of lithium and of alkaline earth metals are suitable for carrying out the present process. Examples which may be mentioned of salts which can be used within the scope of the present invention are the hydroxides, the carbonates, the iodides and the carboxylates, containing at most 12 carbon atoms, of the abovementioned metals. Lithium salts and magnesium salts prove to be more particularly effective. According to a preferred aspect of the present process, a lithium salt is used.

Generally, the carboxylates of the abovementioned metals, which contain at most 12 carbon atoms and preferably at most 4 carbon atoms, are particularly suitable for carrying out the present invention. The acetates, in particular lithium acetate, are especially suitable co-catalysts.

If the monovalent (or divalent) cation of these salts, which are co-catalysts whithin the scope of the present process, is designated by $M_2$, the amount of co-catalyst(s) which is generally present in the reaction medium is such that there are from 0.2 to 50 and preferably from 0.5 to 20 gram ions of $M_2$ per gram atom of nickel.

As indicated above, the process forming the subject of the present invention is carried out in the liquid phase, in a carboxylic acid as the solvent.

The precise nature of the carboxylic acid is not of fundamental importance and the choice from among the carboxylic acids available will be governed chiefly by economic and/or practical considerations. Examples which may be mentioned of carboxylic acids which can be used as solvents within the scope of the present process are acetic acid, propionic acid, butyric acid and benzoic acid.

In general, the carboxylic acid represents from 10 to 90% and preferably from 20 to 80% of the volume of the reaction liquid.

As indicated hereinabove, the present reaction is carried out in the liquid phase, under a pressure above atmospheric pressure. In general, it is carried out under a total pressure of more than 15 bars; it serves no purpose, however, to reach 700 bars. To carry out the invention satisfactorily, a total pressure of 25 to 200 bars is recommended.

The reaction temperature is generally above 140° C., but it is not necessary to reach 300° C. Good results are obtained within the temperature range from 160° to 220° C.

Carbon monoxide is preferably used in the essentially pure form, as available commercially. However, the presence of impurities, such as carbon dioxide, oxygen, methane and nitrogen, can be tolerated. The presence of hydrogen is not detrimental, even in relatively large proportions.

At the end of the operation, the acetic anhydride obtained is separated from the other constituents of the reaction medium by any suitable method, for example by distillation.

In order to further illustrate the present invention and the advantages thereof, the following specific examples are given, it being understood that same are intended only as illustrative and in no wise limitative. In the examples which follow, RY (%) denotes the number of mols of acetic anhydride determined per 100 mols of methyl acetate introduced.

EXAMPLES 1 to 8

A series of experiments, of which the particular conditions and also the results are shown in Table (I) below, were carried out using the equipment and procedure described more particularly for Example 8.

The following were introduced into a Hastelloy B2 autoclave with a capacity of 125 ml:
- 25 ml of methyl acetate
- 20 ml of acetic acid
- 80 millimols of methyl iodide
- 8 mg atoms of nickel in the form of nickel acetate tetrahydrate 20 millimols of methyltriphenylphosphonium iodide, which will be designated by MeP(Ph)$_3$I in Table (I) below, and 40 millimols of lithium acetate.

After closing the autoclave, a pressure of 40 bars of carbon monoxide was established. Shaking by means of a reciprocating system was begun and the autoclave was heated to 180° C., over the course of about 20 minutes, by means of an annular furnace. The pressure in the autoclave was then 64 bars; it was kept constant and equal to 70 bars by successively introducing further amounts of carbon monoxide.

After 2 hours at 180° C., the shaking and heating were stopped; the autoclave was cooled and degassed. The reaction medium was then determined: it contained 19.58 g of acetic anhydride. RY (%)=61.

TABLE I

| No. | $P_T$ (bars) | Ionic iodide Nature | millimols | Co-catalyst Nature | millimols | RY (%) |
|---|---|---|---|---|---|---|
| a | 70 | NaI | 20 | — | 0 | 6.5 |
| 1 | 70 | NaI | 20 | Mg(OAc)$_2$ | 20 | 11 |
| 2 | 70 | NaI | 20 | LiOAc | 40 | 13.5 |
| 3 | 70 | NaI | 53 | LiOAc | 40 | 38 |
| b | 70 | MeP(Ph)$_3$I | 20 | — | 0 | 18 |
| 4 | 70 | MeP(Ph)$_3$I | 20 | KOAc | 40 | 30 |
| 5 | 90 | MeP(Ph)$_3$I | 20 | Mg(OAc)$_2$ | 40 | 38 |
| 6 | 70 | MeP(Ph)$_3$I | 20 | LiOAc | 5 | 23 |
| 7 | 70 | MeP(Ph)$_3$I | 20 | LiOAc | 10 | 33 |
| 8 | 70 | MeP(Ph)$_3$I | 20 | LiOAc | 40 | 61 |

In the table above, $P_T$ indicates the total pressure and OAc designates the acetate anion.

In Example 3, the productivity with respect to acetic anydride was 120 grams per hour and liter (g/hour×liter); taking account of the water of hydration in the catalyst, this productivity ("potential productivity") would be 160 g/hour×liter.

In Example 8, the productivity was 200 g/hour×liter and the "potential productivity" would be 230 g/hour×liter.

A comparison of the results obtained in Examples 1 to 3, carried out in the presence of a co-catalyst, with the result obtained in control experiment (a), in which the co-catalyst was omitted, shows the beneficial effect of the co-catalyst in the reaction in question.

The same conclusion can be drawn from a comparison of the results of Examples 4 to 8 with the result obtained in control experiment (b).

EXAMPLE 9 AND CONTROL EXPERIMENTS (c) AND (d)

Using the equipment and the procedure described above, a second series of experiments were carried out on a charge comprising:

12.5 ml of methyl acetate
11.25 ml of acetic acid
19 millimols of methyl iodide and
5 mg atoms of nickel in the form of nickel tetracarbonyl.

The particular conditions and also the results obtained at a temperature of 180° C., under a total pressure kept at 70 bars by introducing further amounts of carbon monoxide, are shown in Table II below, in which t designates the duration of the experiment at the abovementioned temperature.

TABLE II

| No. | t in hours | Ionic iodide Nature | millimols | Co-catalyst Nature | millimols | RY (%) |
|---|---|---|---|---|---|---|
| c | 4 | NaI | 25 | — | 0 | 50 |
| d | 4 | — | 0 | LiI | 45 | 15 |
| 9 | 1 | NaI | 25 | LiI | 20 | 22 |

EXAMPLE 10

Example 2 above was repeated, the sodium iodide being replaced by potassium iodide and the total pressure being 90 bars.

RY (%)=9.2

Potential productivity: 60 g/hour×liter.

EXAMPLE 11

Example 2 above was repeated, the sodium iodide being replaced by cesium iodide.

RY (%)=4

Potential productivity: 45 g/hour×liter.

EXAMPLE 12

Example 2 above was repeated, the acetic acid being replaced by 20 g of benzoic acid.

RY (%)=33.

EXAMPLE 13

Example 8 above was repeated, the acetic acid being replaced by 20 g of benzoic acid and the total pressure being 90 bars.

RY(%)=70.5 (which corresponds to a productivity of 220 g/hour×liter).

EXAMPLE 14

Using the autoclave and the procedure described above, an experiment was carried out on a charge consisting of:

25 ml of methyl acetate
20 ml of acetic acid
80 millimols of methyl iodide
8 mg atoms of nickel in the form of nickel tetracarbonyl
50 millimols of sodium iodide and
50 millimols of lithium acetate.

The results obtained after a reaction time of 2 hours at 180° C., with the total pressure being kept at 60 bars by introducing further amounts of carbon monoxide, were as follows:

RY (%)=42 (which corresponds to a productivity of 130 g/hour×liter).

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A process for the preparation of acetic anhydride which comprises carbonylating methyl acetate in the liquid phase, in a carboxylic acid which represents from about 10 to about 90% by volume of the reaction liquid, in the presence of an effective amount of nickel, methyl iodide, an ionic iodide, and a co-catalyst, the ionic iodide being selected from the group consisting of quaternary ammonium iodides, quaternary phosphonium iodides, sodium iodide, potassium iodide and cesium iodide when the co-catalyst is a lithium salt, and the ionic iodide being selected from the group consisting of sodium iodide, potassium iodide and cesium iodide when the co-catalyst is an alkaline earth metal salt, at a total pressure between about 25 and about 200 bars.

2. A process according to claim 1, wherein the temperature is between about 140° and about 300° C.

3. A process according to claim 1, wherein the temperature is between about 160° and about 220° C.

4. A process according to claim 1, wherein the concentration of the nickel is between about 5 and about 2000 milligram atoms per liter of reaction medium.

5. A process according to claim 1, wherein the concentration of the nickel is between about 20 and about 1000 milligram atoms per liter of reaction medium.

6. A process according to claim 1, wherein the methyl iodide is present in the reaction medium in an amount of from about 1 to about 100 mols per gram atom of nickel.

7. A process according to claim 1, wherein the methyl iodide is present in the reaction medium in an amount of from about 3 to about 50 mols per gram atom of nickel.

8. A process according to claim 1, wherein the molar ratio $M_1/Ni$, wherein $M_1$ represents the cation of the ionic iodide, is between about 0.5 and about 100.

9. A process according to claim 1, wherein the molar ratio $M_1/Ni$, wherein $M_1$ represents the cation of the ionic iodide, is between about 0.8 and about 40.

10. A process according to claim 1, wherein the ionic iodide is a quaternary phosphonium iodide.

11. A process according to claim 1, wherein the ionic iodide is sodium iodide.

12. A process according to claim 1, wherein the ionic iodide is potassium iodide.

13. A process according to claim 1, wherein the ionic iodide is cesium iodide.

14. A process according to claim 1, wherein the co-catalyst is a lithium carboxylate or an alkaline earth metal carboxylate.

15. A process according to claim 14, wherein the co-catalyst is an acetate.

16. A process according to claim 1, wherein the co-catalyst is a lithium salt.

17. A process according to claim 16, wherein the co-catalyst is lithium acetate.

18. A process according to claim 1, wherein the molar ratio $M_2/Ni$, wherein $M_2$ represents the cation of the co-catalyst, is between about 0.2 and about 50.

19. A process according to claim 1, wherein the molar ratio $M_2/Ni$, wherein $M_2$ represents the cation of the co-catalyst, is between about 0.5 and about 20.

20. A process according to claim 1, wherein the carboxylic acid is acetic acid.

21. A process according to claim 1, wherein the carboxylic acid is benzoic acid.

22. A process according to claim 1, wherein the carboxylic acid represents from about 20 to about 90% of the volume of the reaction liquid.

23. A process according to claim 1, wherein the ionic iodide is selected from the group consisting of sodium iodide, potassium iodide and cesium iodide.

24. A process according to claim 1, wherein the ionic iodide is selected from the group consisting of quaternary ammonium iodides and quaternary phosphonium iodides.

25. A process according to claim 23, wherein the co-catalyst comprises a lithium salt.

26. A process according to claim 24, wherein the co-catalyst comprises a lithium salt.

* * * * *